United States Patent
Schwartz et al.

(10) Patent No.: US 9,526,476 B2
(45) Date of Patent: Dec. 27, 2016

(54) SYSTEM AND METHOD FOR MOTION TRACKING USING UNIQUE ULTRASOUND ECHO SIGNATURES

(75) Inventors: Benjamin M. Schwartz, Seattle, WA (US); Nathan J. McDannold, Jamaica Plain, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 216 days.

(21) Appl. No.: 14/111,073

(22) PCT Filed: Apr. 10, 2012

(86) PCT No.: PCT/US2012/032900
§ 371 (c)(1),
(2), (4) Date: May 5, 2014

(87) PCT Pub. No.: WO2012/142031
PCT Pub. Date: Oct. 18, 2012

(65) Prior Publication Data
US 2014/0275966 A1 Sep. 18, 2014

Related U.S. Application Data

(60) Provisional application No. 61/474,346, filed on Apr. 12, 2011.

(51) Int. Cl.
*A61B 5/05* (2006.01)
*A61B 8/08* (2006.01)
(Continued)

(52) U.S. Cl.
CPC .......... *A61B 8/5276* (2013.01); *A61B 5/0035* (2013.01); *A61B 5/055* (2013.01); *A61B 5/113* (2013.01);
(Continued)

(58) Field of Classification Search
USPC ........................................................ 600/411
See application file for complete search history.

(56) References Cited

U.S. PATENT DOCUMENTS

| 2005/0271297 A1* | 12/2005 | Zbilut | G06K 9/00523 382/278 |
| 2006/0208730 A1* | 9/2006 | Kozerke | G01R 33/5611 324/307 |
| 2009/0253102 A1* | 10/2009 | Porikli | G09B 23/286 434/6 |

FOREIGN PATENT DOCUMENTS

| JP | 2005144154 A | 6/2005 |
| KR | 20090050423 A | 5/2009 |
| RU | 2226360 C2 | 4/2004 |

OTHER PUBLICATIONS

Deprez et al (3D estimation of soft biological tissue deformation from radio-frequency ultrasound volume acquisitions).*
(Continued)

*Primary Examiner* — Joel F Brutus
(74) *Attorney, Agent, or Firm* — Quarles & Brady LLP

(57) ABSTRACT

A system and method for tracking the position of a region in a subject using an ultrasound system is provided. Training data that indicates the position of the region is acquired from the subject while ultrasound data is acquired from the subject using the ultrasound system. A position mapping table is formed using the training data and ultrasound data; this table relates position information contained in the training data to the acquired ultrasound data. The position of the region is tracked by acquiring additional ultrasound data from the subject using the ultrasound system. This additional ultrasound data is compared to the ultrasound data contained in the position mapping table to identify the position of the region based on a unique relationship between the position of the region and ultrasound echo signatures of the ultra- (Continued)

sound data acquired in both the training and motion tracking stages.

15 Claims, 3 Drawing Sheets

(51) Int. Cl.
    *A61B 5/11*     (2006.01)
    *A61B 5/113*     (2006.01)
    *A61B 8/00*     (2006.01)
    *A61B 5/00*     (2006.01)
    *A61B 5/055*     (2006.01)

(52) U.S. Cl.
    CPC ............. *A61B 5/1126* (2013.01); *A61B 5/721* (2013.01); *A61B 8/08* (2013.01); *A61B 8/085* (2013.01); *A61B 8/4416* (2013.01); *A61B 5/0555* (2013.01); *A61B 5/6892* (2013.01); *A61B 8/4236* (2013.01); *A61B 2562/164* (2013.01)

(56) References Cited

OTHER PUBLICATIONS

McDanoold et al (Magnetic resonance acoustic radiation force imaging).*
Curiel, et al., Progress in Multimodality Imaging: Truly Simultaneous Ultrasound and Magnetic Resonance Imaging, IEEE Transactions on Medical Imaging, 2007, 26(12):1740-1746.
Davies, et al., Ultrasound Quantitation of Respiratory Organ Motion in the Upper Abdomen, British Journal of Radiology, 1994, 67(803):1096-1102.
Feinberg, et al., Hybrid Ultrasound-MRI for Improved Cardiac Imaging and Real Time Respiration Control, Magnetic Resonance in Medicine, 2010, 63(2):290-296.
Gunther, et al., Ultrasound-Guided MRI: Preliminary Results Using a Motion Phantom, Magnetic Resonance in Medicine, 2004, 52(1):27-32.
McDannold, et al., MRI Evaluation of Thermal Ablation of Tumors with Focused Ultrasound, Journal of Magnetic Resonance Imaging, 1998, 8(1):91-100.
Oliveira, et al., Rapid Motion Correction in MR-Guided High-Intensity Focused Ultrasound Heating Using Real-Time Ultrasound Echo Information, NMR in Biomedicine, 2010, 23:1103-1108.
Pernot, et al., 3D Real-Time Motion Correction in High Intensity Focused Ultrasound Therapy, Ultrasound in Medicine and Biology, 2004, 30(9):1239-1249.
Ries, et al., Real-Time 3D Target Tracking in MRI Guided Focused Ultrasound Ablations in Moving Tissues, Magnetic Resonance in Medicine, 2010, 64(6):1704-1712.
Ross, et al., Real-Time Liver Motion Compensation for MRgFUS, Medical Image Computing and Computer-Assisted Intervention—MICCAI 2008, 5242:806-813.
Shakespeare, et al., A Method for Foetal Heart Rate Monitoring During Magnetic Resonance Imaging Using Doppler Ultrasound, Physiological Measurement, 1999, 20(4):363-368.
Tang, et al., Simultaneous Ultrasound and MRI System for Breast Biopsy: Compatibility Assessment and Demonstration in a Dual Modality Phantom, IEEE Transactions on Medical Imaging, 2008, 27(2):247-254.
Viola, et al., A Comparison of the Performance of Time-Delay Estimators in Medical Ultrasound, IEEE Transactions on Ultrasonics, Ferroelectrics and Frequency Control, 2003, 50(4):392-401.
PCT International Search Report and Written Opinion, PCT/US2012/032900, Jul. 12, 2012, 6 pages.

* cited by examiner

SYSTEM AND METHOD FOR MOTION TRACKING USING UNIQUE ULTRASOUND ECHO SIGNATURES

CROSS-REFERENCE TO RELATED APPLICATIONS

This application represents the national stage entry of PCT International Application No. PCT/US2012/032900 filed on Apr. 10, 2012 and claims the benefit of U.S. Provisional Patent Application Ser. No. 61/474,346 filed on Apr. 12, 2011, and entitled "Ultrasound Device and System", both of which are hereby incorporated by reference herein in their entirety and for all purposes.

STATEMENT REGARDING FEDERALLY SPONSORED RESEARCH

This invention was made with government support under RR019703 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for compensating for patient motion during an MRI scan using ultrasound.

Respiratory motion is a major cause of image degradation in abdominal MRI. The artifacts caused by respiratory motion are often alleviated by the use of MRI navigators. In typical MRI navigator techniques, short imaging blocks are used to assess the current respiratory motion phase. These imaging blocks, referred to as navigators, are interleaved between imaging blocks that obtain the images of the subject. Examples of navigators include a pencil beam excitation that crosses the diaphragm, or an image of the liver region obtained using a bright-blood single-shot echoplanar imaging ("EPI") pulse sequence.

Position information is derived from the acquired navigators. This position information may be used to retrospectively compensate for the effects of motion during the image reconstruction process, or to prospectively compensate for the effects of the motion by changing the excitation and readout parameters used during the on-going MRI scan. Navigator techniques can be classified as "gating" techniques if they reject unusable data, or as "motion correcting" techniques if they modify each data acquisition in proportion to the measured position offset. The position information derived from an MRI navigator can also be used to control another real-time system, such as a steerable focused ultrasound ablator.

Navigators often achieve good artifact reduction, but they also have significant costs. Navigators typically slow down the imaging process, can interfere with the maintenance of steady-state magnetization, and require difficult pulse-sequence engineering that may need to be repeated for each combination of navigator type and imaging sequence. It would therefore be desirable to provide a system and method for compensating for subject motion during an MRI scan that overcomes these limitations of relying on MRI navigators.

A number of papers have demonstrated that pulse-receive ultrasound devices can be operated in the MRI environment, and that ultrasound may be used for subject motion compensation. These studies that used ultrasound to compensate for subject motion in MRI disclose directly measuring positions within the subject using ultrasound. In one approach described by P. L. de Oliveira, et al., in "Rapid Motion Correction in MR-Guided High-Intensity Focused Ultrasound Heating Using Real-Time Ultrasound Echo Information," *NMR in Biomedicine*, 2010; (23):1103-1108, a pencil-beam ultrasound transducer was oriented so that the direction of the subject motion was along the axis of the ultrasound beam. In this method, position information was directly computed from shifts observed in the echo delay. The authors of this technique noted that it was not expected to work in vivo because organs, such as the liver, predominantly move in the craniocaudal direction, a direction with which an externally placed ultrasound transducers cannot be aligned, as required by this method.

An attempt to solve the problem of tracking motion along an inaccessible axis was described by M. Pernot, et al., in "3-D Real-Time Motion Correction in High-Intensity Focused Ultrasound Therapy," *Ultrasound in Medicine & Biology*, 2004; 30:1239-1249, in which the direct shift-tracking technique was extended to use three or more ultrasound transducers. In this technique, the ultrasound transducers were widely spaced so that their beams were oriented toward a focal point at large relative angles. The direction of motion was then determined from the shift observed in each transducer. This technique has the advantage of direct displacement measurement, but requires expensive multiple-transducer transmit-receive capabilities, is intrinsically limited to measure simple translations, and will accumulate errors due to velocity integrations in the position estimate, resulting in a drift in the position measurement over time. This technique has not been demonstrated in conjunction with MRI.

A technique that attempted to permit measurement of non-translational motion and to avoid problems associated with cumulative estimators was described by M. Gunther and D. A. Feinberg in "Ultrasound-Guided MRI: Preliminary Results Using a Motion Phantom," *Magnetic Resonance in Medicine*, 2004; 52(1):27-32. In this technique, a linear ultrasound transducer array was used to produce two-dimensional ultrasound images. The position is indicated directly by shifts and rotations observed in these images. This approach was recently demonstrated for in vivo motion compensation in cardiac imaging, as described by D. A. Feinberg, et al., in "Hybrid Ultrasound MRI for Improved Cardiac Imaging and Realtime Respiration Control," *Magnetic Resonance in Medicine*, 2010; 63:290-296. Although this technique is capable of tracking motion along the craniocaudal axis, it requires a substantial investment in ultrasound equipment and electronics. The technique is also limited to measuring motion that occurs within the ultrasound imaging plane, and will not detect small displacements in the through-plane direction. These small displacements that occur in the through-plane direction are important for interventional applications.

Thus, it is desirable to provide a system and method for motion tracking and compensation in MRI and other clinical applications using ultrasound such that motion along multiple different motion axes can be tracked.

SUMMARY OF THE INVENTION

The present invention overcomes the aforementioned drawbacks by providing a system and method for motion tracking with ultrasound that is capable of tracking motion not only along the ultrasound beam axis, but in a plane transverse to the beam axis by using a similarity metric that allows for separation and identification of displacement occurring in these different directions.

It is an aspect of the invention to provide a method for tracking a position of a location-of-interest in a subject using an ultrasound system. Training data is acquired from the subject, the training data indicating a position of the location-of-interest in a subject. Over the same time period as the training data acquisition, ultrasound data is acquired from the subject using an ultrasound system. Using the training data and acquired ultrasound data, a position mapping table is formed. The position mapping table relates position information contained in the training data to the acquired ultrasound data. A position of the location-of-interest is then tracked by acquiring ultrasound data from the subject using the ultrasound system. This acquired ultrasound data is compared to the ultrasound data contained in the position mapping table. This comparison identifies the position of the location-of-interest based on a unique relationship between the position of the location-of-interest and ultrasound echo signatures of the ultrasound data acquired in both the training and motion tracking stages. The ultrasound system includes, for example, not more than one ultrasound transducer.

It is another aspect of the invention to provide an ultrasound motion tracking system that includes an ultrasound system and a processor in communication with the ultrasound system. The ultrasound system includes not more than one ultrasound transducer, and is configured to transmit an ultrasound beam into a volume-of-interest and the receive therefrom ultrasound echo signals. The processor is programmed to receive an ultrasound echo signal from the ultrasound system, calculate a similarity metric by comparing the received ultrasound echo signal to a stored position mapping table that relates position information contained in stored training data with stored ultrasound data that was acquired concurrently with the stored training data, and determine a position of a the volume-of-interest by identifying the position information in the position mapping table that is associated with the stored ultrasound data that results in a calculated similarity metric indicating a closest similarity between the received ultrasound echo signal and the stored ultrasound data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
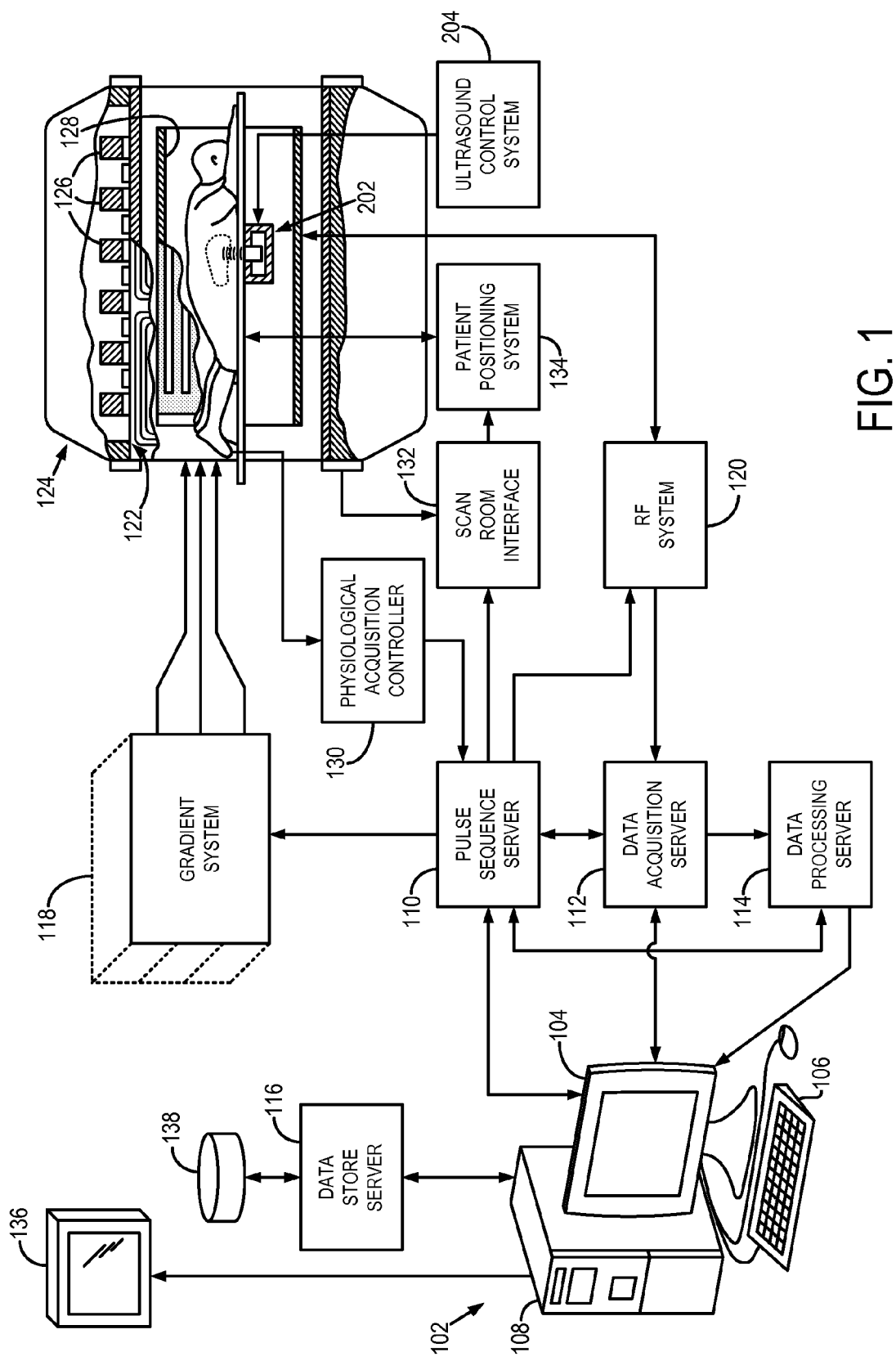
FIG. 1 is a block diagram of an example of a magnetic resonance imaging ("MRI") that is configured to incorporate the ultrasound motion tracking and compensation system of the present invention.

A system and method for ultrasound-based motion tracking and compensation of a medical imaging or other clinical procedure is provided. As one example, ultrasound data is used to achieve prospective motion compensation in magnetic resonance imaging ("MRI"). In general, the system and method take advantage of the uniqueness of ultrasound echo patterns produced by different anatomical locations in a subject. These ultrasound echo patterns may be combined with position information obtained from MRI data during a training stage to form a position mapping table that relates ultrasound measurements to unique positions in the subject's tissue. During prospective correction, ultrasound measurements are frequently obtained and correlated with the position mapping table to determine the corresponding position information. The present invention is particularly well-suited for respiratory motion compensation during interventional MRI procedures in moving organs, such as the liver.

In one configuration, a single MRI-compatible ultrasound transducer is placed against a subject's skin, such as adjacent the subject's abdomen. The ultrasound transducer is operated to produce a pencil-beam ultrasound field that is oriented along a direction that is angled with respect to the longitudinal axis of the MRI system. For example, the ultrasound field is oriented along a direction that is angled at substantially ninety degrees with respect to the longitudinal axis of the MRI system. As an example, this direction may be approximately oriented along the dorsal direction of the subject. Preferably, the ultrasound transducer is positioned such that the ultrasound field passes near the center of a volume-of-interest.

The present invention differs from previous attempts at using ultrasound for motion compensation in MRI because in the present invention obtains ultrasound data that does not directly indicate tissue position. Instead, the present invention makes use of the advantage that ultrasound echoes observed at different anatomical locations in a subject are distinctly and uniquely identifiable.

The ultrasound measurements obtained with the system and method of the present invention may be described as a "biometric ultrasound navigator," by analogy to biometric identifiers such as fingerprints and iris scans. Like a fingerprint or an iris scan, an ultrasound echo contains a pattern produced by stochastic biological processes that occur during gestational development. In both cases, a training process is required to relate the raw biometric data to the desired information. In both cases, the process relies on uniqueness: each tissue position exhibits a distinct biometric signature.

This method provides an indirect measurement of tissue position. The method requires a training period to determine the correspondence between the measured ultrasound echoes and the actual anatomical positions. The method is therefore constrained by the contents of the training data; that is, the training data determines the accuracy of the motion tracking and compensation. The biometric uniqueness of the ultrasound echoes allows the training data to be effective. Without biometric uniqueness, the system cannot detect when the training data are no longer applicable, which may occur if the patient moves laterally or the tissue undergoes any unanticipated shift.

Biometric navigation is different from other position measurement methods by its use of a unique identifier derived from the tissue at each location. This unique identifier does not directly indicate a position, but its biometric uniqueness ensures that once a position is associated with a particular identifier, the position will not be indicated spuriously. The uniqueness of the identifier representing each location is due to the large entropy of the high-dimensional space from which biometric patterns are randomly drawn.

In the case of ultrasound navigators, entropy is provided by reflections from macroscopic anatomical structures and by sound scattered off of countless microstructures. The resulting interference pattern is termed speckle, and is well approximated by a broadband Gaussian random field that does not change with time, unless the relevant microstructures are moved or altered. The entropy of ultrasound navigators can be estimated by considering only the speckle and by applying the Shannon-Hartley channel capacity theorem for a noisy channel:

$$C = B \log_2(1+\text{SNR}) \quad (1);$$

where C is a channel capacity, B is the ultrasound transducer bandwidth, and SNR is signal-to-noise ratio. A typical ultrasound transducer may have a bandwidth, B, of at least 1.5 MHz and SNR of at least three. Note that although speckle is often regarded as noise, in this instance the time-invariant speckle is treated as signal. From these parameters, a channel capacity of 3 megabits per second, or 4 bits per millimeter, can be achieved in pulse-echo ultrasound. By way of comparison, a typical iris scan has an effective entropy of 3.2 bits per millimeter-squared. With this biometric ultrasound navigator method, a target region that is 20 millimeters in size would have an entropy of 80 bits, or a collision probability of $1 \times 10^{-24}$. It is this strong expectation of uniqueness that provides the ability to reliably correlate ultrasound navigator echoes to particular anatomical positions.

In this method, the unique identifier takes the form of an ultrasound echo transverse to the axis of motion, windowed in depth so that the data correspond to a specific volume of interest. The distinct identifiability of echoes at each position may be provided by macroscopic anatomical structures, or by microscopic tissue structures whose scattering fields interfere to form speckle.

This method utilizes the assumption that the ultrasound properties of a volume of tissue are highly repeatable over the course of an imaging session. To the extent that this assumption holds true, biometric navigation can reliably function during arbitrary repetitive motions, even if the pattern includes non-rigid deformations that alter the speckle pattern.

Motion Tracking and Compensation Method

It is an aspect of the present invention to provide a method for motion tracking and compensation during an MRI scan that includes determining tissue positions by applying a dissimilarity function to the ultrasound data. This approach allows motion tracking to be performed by a single ultrasound transducer that is oriented orthogonal to the principal axis of motion. Existing ultrasound tracking systems either require a large array of transducers or require that the transducer be oriented parallel to the direction of motion.

A dissimilarity function, D(U,V), between two ultrasound signals, U(t) and V(t), may be defined as follows:

$$D^2(U, V) = \min_{\Delta t} \int_{-\infty}^{+\infty} (W(t)U(t) - W(t+\Delta t)V(t+\Delta t))^2 \, dt \quad (2)$$

By this definition, D is the minimum Euclidean distance between U and any shifted copy of V, where both U and V are windowed by multiplication with a window function, W. Minimizing across a range of time shifts, $\Delta t$, is important because it allows the separation of transverse displacements across the ultrasound beam from longitudinal displacements along the beam axis. The ultrasound signals are rapidly varying functions of time, so a small shift in time results in a large difference between the two otherwise identical signals.

Ultrasound signals are received by a transducer and sampled, after which a fixed range of samples corresponding to the interior of the object being monitored is selected. By way of example, an ultrasound signal may be sampled at a rate of 100 MSa/s. The dissimilarity function described in Eqn. (2) may be discretized as follows:

$$d^2(u, v) = \min_s \sum_i (w_i u_i - w_{i+s} v_{i+s})^2 \quad (3)$$

where w is a rectangular window corresponding to the selected range of samples. The minimization in Eqn. (3) may be optimized for real-time applications, such as prospective motion compensation. For real-time applications, the dissimilarity between newly acquired ultrasound signals and data entries in the mapping table must be quickly calculated. This faster computation can be achieved with the following formulation of Eqn. (3):

$$d^2(u, v) = P + Q - 2\max_s R_s; \quad (4)$$

where $$P = \sum_{j=0}^{N-1} x_j^2; \quad (5)$$

$$Q = \sum_{k=0}^{N-1} v_k^2; \quad (6)$$

and $$R_s = \sum_{i=-\min(s,0)}^{N-\max(s,0)-1} x_i y_{i+s}. \quad (7)$$

It is noted that the computation in Eqn. (7) can be performed efficiently because it is essentially the cross-correlation between to vectors, x and y:

$$R_s = (x \star y)_s \quad (8);$$

which, by the Fourier cross-correlation theorem may be rewritten as the following:

$$R = FT^{-1}\{FT\{x\}^* \cdot FT\{y\}\} \quad (9);$$

where $FT\{\ldots\}$ and $FT^{-1}\{\ldots\}$ are the discrete Fourier transform and discrete inverse Fourier transform, respectively, and where $(\ldots)^*$ is the complex conjugate operation.

The ultrasound properties of human tissues are complex; thus, it may be beneficial to modify the dissimilarity measure of Eqns. (2) and (3), for example, by deriving the dissimilarity measure from the displacement tracking techniques developed for ultrasound elastography and Doppler imaging.

Using this dissimilarity measure, motions across the beam axis (transverse motions), motions along the beam axis (longitudinal motions), or a combination of both can be reliably correlated to unique ultrasound echo signatures. The dissimilarity measure provided in Eqns. (2) and (3) is a shift-invariant similarity metric, where the shift corresponds to longitudinal displacements. When displacements along the longitudinal axis are of interest, a partially shift-invariant similarity metric is used, in which the metric's insensitivity to shift is reduced, but not eliminated. This is easily achieved, for example, by modifying Eqn. (3) as follows:

$$d^2(u, v) = \min_s \sum_i (w_i u_i - w_{i+s} v_{i+s})^2 + \alpha s^2; \qquad (10)$$

where alpha is a constant representing the strength of the sensitivity to shift. It is contemplated that a partially shift-invariant metric of this kind can produce correct tracking for all mixed and longitudinal motions, as well as all transverse motions.

At short distances, such as below 0.5 mm, the squared dissimilarity is linearly related to the squared distance. At larger distances, such as those above 2 mm, the dissimilarity saturates and becomes constant. These behaviors are as expected from a simple model of ultrasound echogenicity, in which the signal changes smoothly on scales smaller than the ultrasound beam width, but becomes uncorrelated at distances larger than the beam width, such as a beam width of 2 mm for the examples provided above. Any dissimilarity at zero distance is likely due to factors such as thermal and electrical noise that decrease the similarity of successive measurements even if the location is unchanged. Using the examples provided above, an appropriately chosen dissimilarity threshold may reject all pairs separated by more than 2 mm and may accept all pairs separated by less than 0.5 mm. This is sufficient to enable reliable matching.

MRI System

Referring particularly now to FIG. 1, an example of a magnetic resonance imaging ("MRI") system 100 that incorporates an ultrasound motion tracking and compensation system 200 is illustrated. As will be described in more detail below, the ultrasound motion tracking and compensation system 200 generally includes an ultrasound system 202 and an ultrasound control system 204 including pulse-echo circuitry that controls the ultrasound system 202 to transmit an ultrasound beam and to receive echo signals.

The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radio frequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil, are received by the RF system 120 and digitized under direction of commands produced by the pulse sequence server 110. The RF system 120 includes an RF transmitter (not shown in FIG. 1) for producing a wide variety of RF pulses used in MR pulse sequences. The RF transmitter is responsive to the scan prescription and direction from the pulse sequence server 110 to produce RF pulses of the desired frequency, phase, and pulse amplitude. The generated RF pulses may be applied to the whole body RF coil 128 or to one or more local coils or coil arrays.

The RF system 120 also includes one or more RF receiver channels. Each RF receiver channel may include an RF amplifier that amplifies the MR signal received by the coil 128 to which it is connected, and a detector that may, for example, detect and digitize the I and Q quadrature components of the received MR signal. The magnitude of the received MR signal may thus be determined at any sampled point by the square root of the sum of the squares of the I and Q components:

$$M = \sqrt{I^2 + Q^2} \qquad (11)$$

and the phase of the received MR signal may also be determined:

$$\varphi = \tan^{-1}\left(\frac{Q}{I}\right). \qquad (12)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110.

The data processing server 114 receives MR data from the data acquisition server 112 and processes it in accordance with instructions downloaded from the workstation 102. Such processing may include, for example: Fourier transformation of raw k-space MR data to produce two or three-dimensional images, application of filters to a reconstructed image, or the like.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real-time images may be stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Motion Tracking and Compensation System

Figure 2:
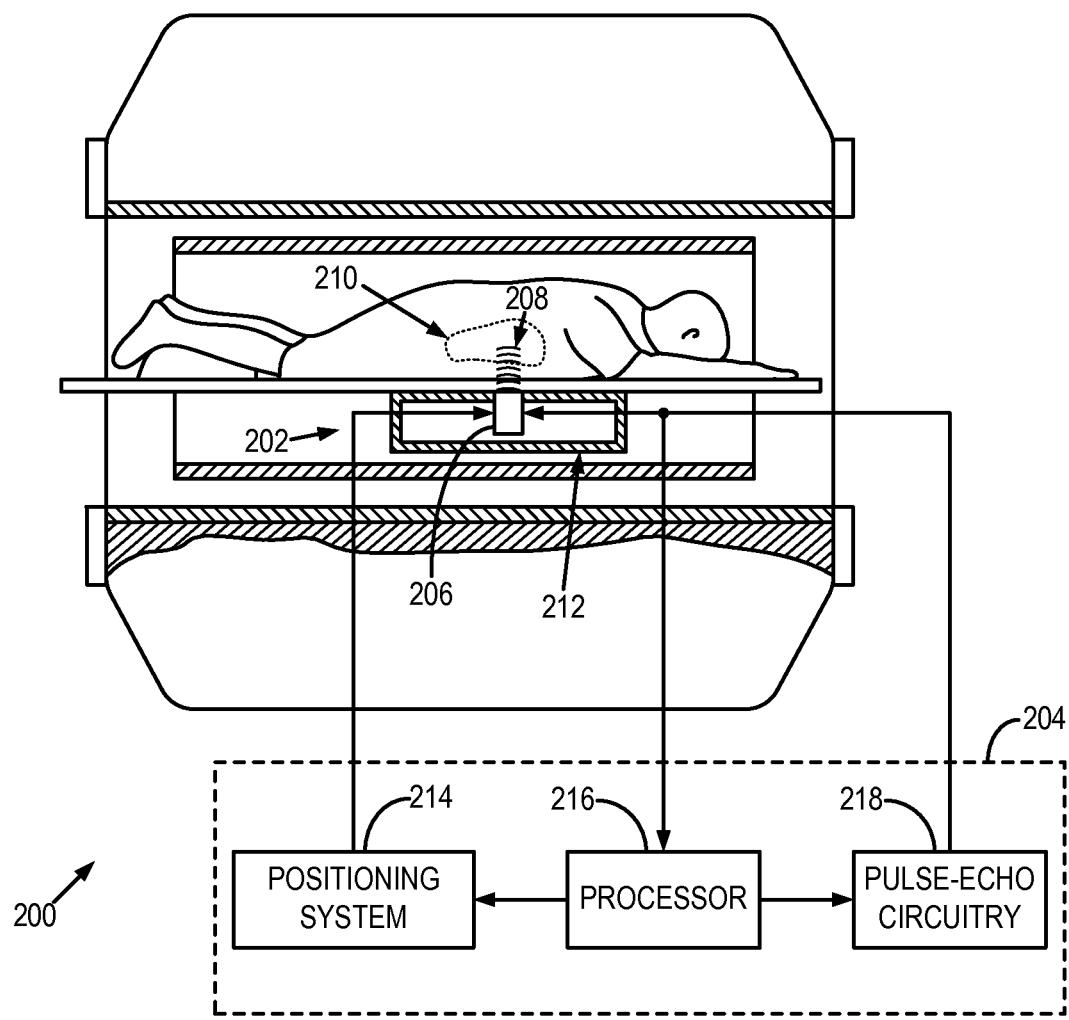
FIG. 2 is a block diagram of an example of an ultrasound motion tracking and compensation system.

Referring now to FIG. 2, an example of an ultrasound motion tracking and compensation system 200 is illustrated. Although this example of the ultrasound motion tracking and compensation system 200 illustrates its use in connection with an MRI system, it will be appreciated by those skilled in the art that the ultrasound motion tracking and compensation system 200 may also be used with other medical imaging systems, with physiological data acquisition systems, with radiotherapy systems, with stereotactic surgery systems, and in general clinical applications. The ultrasound motion tracking and compensation system 200 tracks the position of a location-of-interest in a subject, such as a patient's organs. An example of this is the tracking of liver motion due to a patient's breathing. The ultrasound motion tracking and compensation system 200 determines positions of the location-of-interest by using a similarity function on acquired ultrasound echo signals, and is configured to track motion using a single ultrasound transducer that is oriented orthogonal to the principal axis of motion. Previous ultrasound tracking systems have either required a large array of transducers or required that the ultrasound transducer be oriented parallel to the direction of motion.

The ultrasound motion tracking and compensation system 200 generally includes an ultrasound system 202 that is controlled by an ultrasound control system 204. The ultrasound system 202 includes an ultrasound transducer 206 that is configured to transmit an ultrasound beam 208 to a volume-of-interest 210 in a subject. By way of example, the ultrasound transducer 206 is a single-element ultrasound transducer that transmits a pencil-beam ultrasound field into the volume-of-interest 210. The ultrasound transducer 206 is also configured to receive echo signals from the volume-of-interest 210 in response to the transmitted ultrasound beam 208.

The ultrasound transducer 206 is preferably placed in direct or nearly direct contact with the subject. For example, the ultrasound transducer 206 may be coupled to an adhesive patch that is placed on the subject's skin. As another example, the ultrasound transducer 206 may form a part of a relatively thin pad that can be placed between an imaging table and the subject. In such a configuration, the relatively thin pad may be on the order of one centimeter in thickness. As yet another example, the ultrasound transducer 206 may be integrated into a focused ultrasound ablator.

In other configurations, the ultrasound transducer 206 may be housed in an enclosure 212 to provide an interface with the subject such that the ultrasound beam 208 can be efficiently transferred from the ultrasound transducer 206 to the subject. By way of example, the enclosure 212 may be filled with an acoustic coupling medium, which allows for a more efficient propagation of ultrasound energy than through air. Exemplary acoustic coupling media include water, such as degassed water.

The top of the enclosure 212 may include a flexible membrane that is substantially transparent to ultrasound, such as a flexible membrane composed of Mylar, polyvinyl chloride ("PVC"), or other plastic materials. In addition, a fluid-filled bag (not shown) that can conform easily to the contours of a patient placed on the table may also be provided along the top of the patient table.

Thus, the ultrasound transducer 206 may be connected to a positioning system 214 that provides movement of the transducer 206 within the enclosure 212, and consequently mechanically adjusts the focal zone of the transducer 206. For example, the positioning system 214 may be configured to move the transducer 206 within the enclosure 212 in any one of three orthogonal directions, and to pivot the transducer 206 about a fixed point within the enclosure 212 to change the angle of the transducer 206 with respect to a horizontal plane.

The ultrasound controller 204 generally includes the positioning system 214, a processor 216, and pulse-echo circuitry 218. The pulse-echo circuitry 218 is configured to provide a driving signal that directs the ultrasound transducer 206 to generate the ultrasound beam 208. When the ultrasound motion tracking and compensation system 200 is used during an MRI scan, the ultrasound controller 204 can be positioned inside or outside of the magnet room of the MRI system.

The processor 216 receives ultrasound echo signals from the ultrasound transducer 206. As described above in detail, received ultrasound echo signals are used to generate a position mapping table during a training stage of a motion tracking and compensation method, and are compared to the position mapping table during a motion tracking and compensation stage of the motion tracking and compensation method. The processor 216 is also in communication with the positioning system 214, and is configured to direct the positioning system 214 to move the position of the ultrasound transducer 206 so that the ultrasound beam 208 will be transmitted to a desired location in the volume-of-interest 210.

The ultrasound transducer 206 may be a single-element ultrasound transducer. By way of example, the ultrasound transducer 206 may be a broadband piston-type ultrasound transducer with a nominal center frequency of 5 MHz and diameter of 4-8 mm. In some configurations, the ultrasound transducer 206 is configured to be highly sensitive to lateral or unexpected motions. Although this sensitivity is not desirable for all imaging applications, it is a valuable safety feature in focused ultrasound surgery applications, where it is crucial to instantly detect any unexpected displacement of the subject being treated. Thus, the ultrasound transducer 206 may be designed for high sensitivity to lateral shifts, consistent with a focal width, for example, of 2 mm. For applications in which lower sensitivity to lateral shifts is desirable, the focus of the ultrasound transducer 206 can be altered by changing the transducer's geometry.

The ultrasound transducer 206 may also include a multi-transducer system, in which only one of the transducers is operated at any one instance. For example, the transducer in the multi-transducer system that appears to be positioned as desired with respect to the volume-of-interest 210 may be operated to transmit the ultrasound beam 208 and to receive echo signals from the volume-of-interest 210. In another configuration, multiple ultrasound transducers 206 may be employed to obtain independent measurements. For example, each of the multiple transducers would be used to transmit its own ultrasound beam and to receive ultrasound echoes formed in response to that beam. These independent measurements could then be grouped together into a composite ultrasound signal that could be used to form a position mapping table, or for comparison to ultrasound data already in a position mapping table.

When used for motion tracking and compensation during an MRI scan, it is preferable that the ultrasound transducer 206 be composed of MRI-compatible materials. In doing so, undesirable MR signal losses in the vicinity of the ultrasound transducer 206 can be mitigated.

Figure 3:
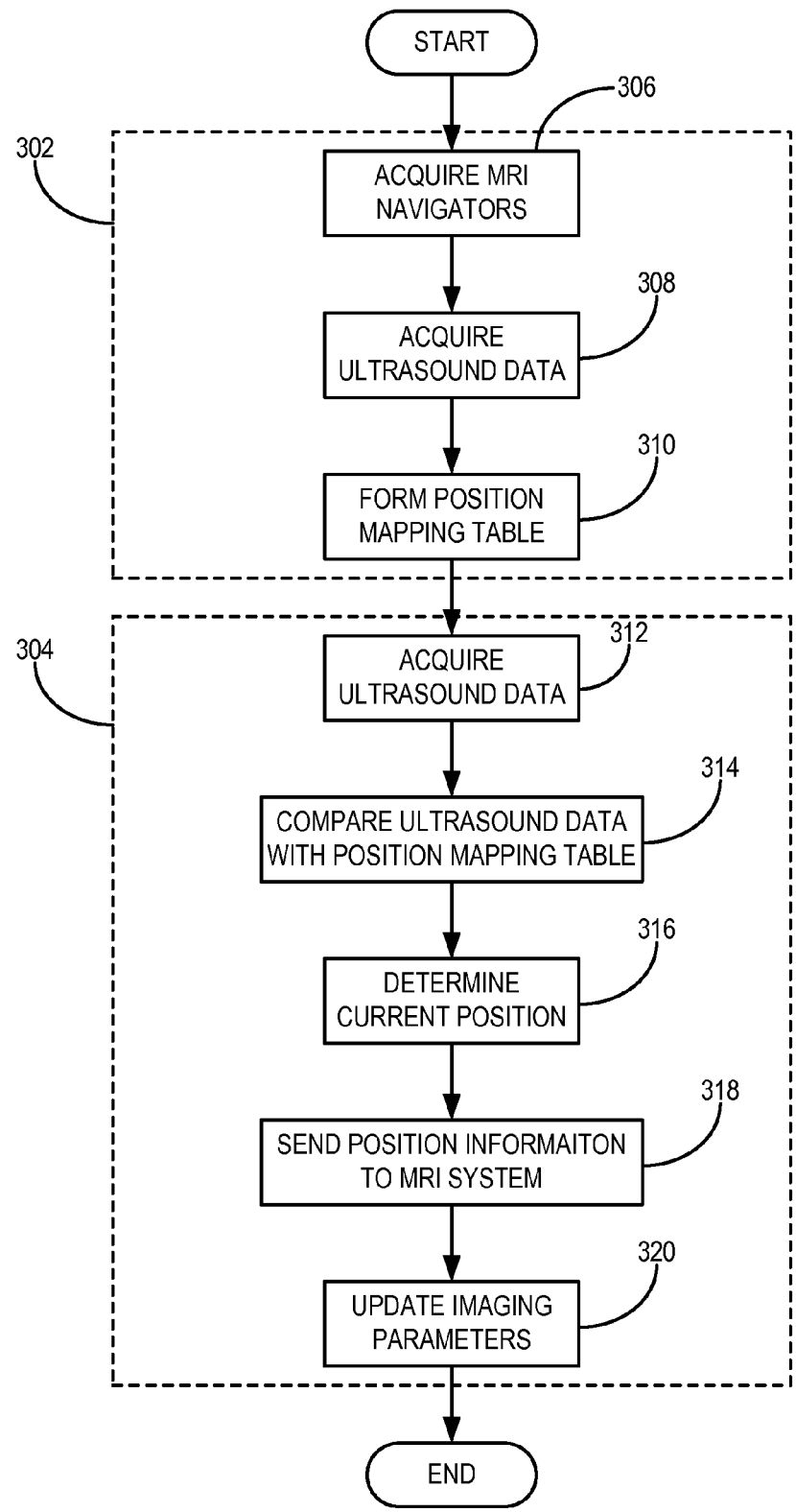
FIG. 3 is a flowchart setting forth the steps of an example of a method for tracking the motion of a region-of-interest using an ultrasound system.

Referring now to FIG. 3, a flowchart setting forth the steps of an example of a method for motion tracking and compensation of an MRI scan using an ultrasound motion tracking and compensation system is illustrated. The method includes two general stages: a training stage 302 and a motion tracking and compensation stage 304. In the training stage 302, an MRI navigator that indicates all desired position information is configured to run continuously. Training data may also be acquired using an imaging modality other than MRI. For example, position information that indicates the position of a location-of-interest may be derived from data acquired with an x-ray imaging system, an x-ray computed tomography ("CT") imaging system, or an ultrasound imaging system, such as an ultrasound imaging system that uses an ultrasound transducer array. An example of an ultrasound transducer array may contain the ultrasound transducer to be used for motion tracking. Generally, the training period should be long enough to ensure that the entire range of anticipated motion is densely sampled; thus, the training stage 302 typically spans multiple motion cycles. During the training stage 302, an ultrasound system will acquire ultrasound data synchronously with MRI data, resulting in a database of paired MRI and ultrasound data. During the motion tracking and compensation stage 304, the ultrasound system will acquire ultrasound data and calculate positions using the database produced during the training stage. The present invention thereby enables the estimation of the current position of a location in a subject during an MRI scan without using any MRI time and without altering the steady state magnetization.

The training stage 302 includes the acquisition of MRI navigators from a volume-of-interest in a subject, as indicated at step 306. During the time in which the MRI navigators are being acquired, ultrasound echo signals are also acquired, as indicated at step 308. By way of example, the MRI control electronics may produce an external trigger pulse at the beginning of each MRI navigator block. This pulse can be used to trigger the acquisition of an ultrasound echo by the ultrasound system. Each ultrasound echo is recorded for later analysis, as are the corresponding MRI navigator data.

Once all of the training data are recorded, the ultrasound and MRI data are combined to form a position mapping table, as indicated at step 310. The position mapping table contains a set of ultrasound measurements and their corresponding positions as determined by the MRI navigators. In some instances, it may be desirable to limit the number of entries in the position mapping table to increase the computational efficiency of the method. In these cases, a representative subset of measurements is selected during the training period for use in the mapping table. During the training stage, it may be advantageous to have the subject breathe deeply in order to ensure that a more complete range of motion is observed.

Now, during the motion tracking and compensation stage 304, ultrasound data is acquired during an MRI scan of the subject, as indicated at step 312. In this MRI scan, no MRI navigators need to be acquired. As indicated at step 314, each received ultrasound echo signal is compared to each entry in the position mapping table. By way of example, the received ultrasound echo signals are compared with the position mapping table using the dissimilarity metric presented above in Eqns. (2) and (3). The current position estimate of the volume-of-interest is the determined as the position indicated by the most the most similar entry in the position mapping table, as indicated at step 316. Once a position estimate has been determined, it may be transmitted to the pulse sequence program running on the MRI scanner, as indicated at step 318. The pulse program then changes its imaging parameters as needed to center on the new position, as indicated at step 320. In some instances, the transmitted position information includes a three-dimensional vector that indicates the center of the imaging volume and a rotation matrix indicating the slice coordinate system. However, in other instances, the transmitted position information may include more, less, or different position information.

Optionally, the position mapping table may be updated during the motion tracking and compensation stage 304. For example, when motion tracking is occurring during an MRI scan, data acquired by the MRI system can be used to update the position mapping table. By way of example, image data may be acquired with an MRI system by performing a gradient-echo pulse sequence with the frequency encoding axis being oriented along the direction of motion. In this instance, the pulse sequence will sometimes acquire one acquisition with no phase encoding, which can be used as navigator data. Thus, if the ultrasound system is synchronized with the MRI system, a new independent position estimate can be computed from the zero phase-encoding acquisition.

An ultrasound motion tracking and compensation system may also be configured to initiate an update to the position mapping table after each new ultrasound data acquisition that results in a positive identification of a position estimate. If the ultrasound system determines that an update is likely to improve the subsequent accuracy or reliability of motion compensation, the update may proceed by adding a new entry to the position mapping table, removing an entry from the position mapping table, modifying an entry in the position mapping table, or combinations of these actions. Possible updates include replacing the least recently used entry with newly measured data and replacing a pre-existing entry that is most similar to the new data by a weighted average of that entry and the new data. Possible methods for determining whether an update is likely to improve the subsequent accuracy include retrospective simulation of the updated position mapping table with previously acquired ultrasound data and heuristic computations that produce similar decisions using less CPU time.

It is contemplated that this system and method for motion tracking and compensation of the present invention will be advantageous for numerous different applications. Examples of the potential applications include monitoring subject motion during focused ultrasound surgery of the liver during free-breathing, cardiac gating of medical imaging scans, respiratory gating medical imaging scans, motion correction in radiotherapy and stereotactic surgery, and other general applications in which physiological data are recorded in the presence of potentially undesirable subject motion. This technique may also have applications for MRI thermometry and other dynamic imaging in the abdomen during free breathing.

Additional examples of where the present invention may be useful include when using static or adaptive procedures to achieve zero latency, synthesis of data from multiple ultrasound transducers, and combining database-driven transverse positioning with cross-correlation longitudinal shifts to measure three-dimensional displacement with a single ultrasound transducer. Another example application of the present invention is using an ultrasound transducer with varying thickness that produces a spatially-encoded frequency response to achieve a specific and tunable sensitivity to motion over a larger volume. Another example application of the present invention is to replace or augment a respiratory bellows system in any clinical application.

Additional examples of where the present invention may be useful for MRI applications include using estimates of the derivatives of position (e.g., velocity and acceleration) to improve the correction of phase artifacts, estimating motion by linear or nonlinear filtering of estimated positions, and estimating motion by computing the similarity of temporally near ultrasound echoes.

Additional examples of where the present invention may be useful for medical imaging applications and other clinical applications include identifying when a subject has shifted from an initial position.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for tracking a position of a location-of-interest in a subject using an ultrasound system, the steps of the method comprising:
   a) acquiring training data from the subject that indicates a position of a location-of-interest in a subject;
   b) acquiring ultrasound data from the subject using an ultrasound system while the training data is acquired in step a);
   c) forming a position mapping table that relates position information contained in the training data acquired in step a) to the ultrasound data acquired in step b);
   d) tracking a position of the location-of-interest in the subject by:
      i) acquiring ultrasound data from the subject using the ultrasound system; and
      ii) calculating a shift-invariant similarity metric and a partially shift-invariant similarity metric by comparing the ultrasound data acquired in step d)i) to the ultrasound data contained in the position mapping table so as to identify a position of the location-of-interest based on a relationship between the position of the location-of-interest and ultrasound echo signatures of the ultrasound data acquired in steps b) and d)i) and to separate motion of the location-of-interest that occurs in a plane transverse to an ultrasound beam axis from motion of the location-of-interest that occurs along the ultrasound beam axis.

2. The method as recited in claim 1 in which the ultrasound data is acquired using an ultrasound system that includes not more than one ultrasound transducer.

3. The method as recited in claim 2 in which the not more than one ultrasound transducer is a single-element ultrasound transducer.

4. The method as recited in claim 1 in which step d)ii) includes calculating a metric that indicates a similarity between the ultrasound data acquired in step d)i) and the ultrasound data contained in the position mapping table formed in step c).

5. The method as recited in claim 4 in which step d)ii) includes windowing the ultrasound data acquired in step d)i) and the ultrasound data contained in the position mapping table with a window function.

6. The method as recited in claim 4 in which step d)ii) includes minimizing an objective function that calculates a Euclidean distance between ultrasound signals.

7. The method as recited in claim 6 in which step d)ii) includes minimizing the objective function over a range of time shifts.

8. The method as recited in claim 1 in which the training data comprises navigator data and step a) includes acquiring the navigator data with a magnetic resonance imaging (MRI) system.

9. The method as recited in claim 1 in which the location-of-interest is at least one of an organ and a tissue.

10. An ultrasound motion tracking system, comprising:
   an ultrasound system including not more than one ultrasound transducer, the ultrasound system being configured to transmit an ultrasound beam into a volume-of-interest and the receive therefrom ultrasound echo signals;
   a processor in communication with the ultrasound system and programmed to:
      receive an ultrasound echo signal from the ultrasound system;
      calculate a shift-invariant similarity metric and a partially shift-invariant similarity metric by comparing received ultrasound echo signal to a stored position mapping table that relates position information contained in stored training data with stored ultrasound data; and
      determine a position of a the volume-of-interest by identifying the position information in the stored position mapping table that is associated with the stored ultrasound data that results in a calculated similarity metric indicating a closest similarity between received ultrasound echo signal and the stored ultrasound data.

11. The ultrasound motion tracking system as recited in claim 10 in which the not more than one ultrasound transducer is a single-element ultrasound transducer.

12. The ultrasound motion tracking system as recited in claim 10 in which the processor is programmed to window the received ultrasound signal and the ultrasound data contained in the stored position mapping table with a window function.

13. The ultrasound motion tracking system as recited in claim 10 in which the processor is programmed to calculate a similarity metric by minimizing an objective function that calculates a Euclidean distance between the received ultrasound signal and the stored ultrasound data.

14. The ultrasound motion tracking system as recited in claim 13 in which the processor is programmed to minimize the objective function over a range of time shifts so as to separate motion of the volume-of-interest that occurs in a plane transverse to an ultrasound beam axis from motion of the volume-of-interest that occurs along the ultrasound beam axis.

15. The ultrasound motion tracking system as recited in claim 10 in which the stored training data comprises navigator data acquired with a magnetic resonance imaging (MRI) system.

* * * * *